United States Patent [19]

Karlsson

[11] Patent Number: 4,614,181
[45] Date of Patent: Sep. 30, 1986

[54] HINGE FOR KNEE JOINT BANDAGE

[75] Inventor: Thomas Karlsson, Stockholm, Sweden

[73] Assignee: Rehband Anatomiska AB, Stockholm, Sweden

[21] Appl. No.: 669,205

[22] Filed: Nov. 7, 1984

[30] Foreign Application Priority Data

Nov. 8, 1983 [SE] Sweden .................. 8306138

[51] Int. Cl.⁴ ............................ A61F 5/01
[52] U.S. Cl. .................. 128/80 C; 128/80 F
[58] Field of Search .......... 128/80 C, 80 F; 16/363, 16/375, 374; 3/22, 30

[56] References Cited

U.S. PATENT DOCUMENTS

| 1,772,601 | 8/1930 | Dunham | 128/80 C |
| 3,174,179 | 3/1965 | Benson | 16/375 |
| 3,825,357 | 7/1974 | Hilton | 3/22 |
| 4,088,130 | 5/1978 | Applegate | 3/22 |
| 4,320,747 | 3/1982 | Daniell, Jr. | 3/22 |
| 4,340,041 | 7/1982 | Frank | 128/80 C |

FOREIGN PATENT DOCUMENTS 513869  6/1955  Canada .................. 128/80 F

Primary Examiner—Edgar S. Burr
Assistant Examiner—Tonya Eckstine
Attorney, Agent, or Firm—Pollock, Vande Sande & Priddy

[57] ABSTRACT

A hinge for knee joint bandages comprising two elongated flat links (3,4) connected for mutual pivoting. At the end portion of one link (4) there are four holes (19-22) distributed along a circular arc symmetrically in relation to the longitudinal axis. A stop pin (16) is inserted in one of the holes to limit the end position of the pivoting movement of the links. The stop pin cooperates with a circular arcuate slot of the other link (3). The slot is greater than 180° and is symmetrically located in relation to the longitudinal axis of the link (3), whereby the hinge can be used either on the inside or the outside of the knee for the adjustment of the desired maximum angular pivoting of the knee.

6 Claims, 5 Drawing Figures

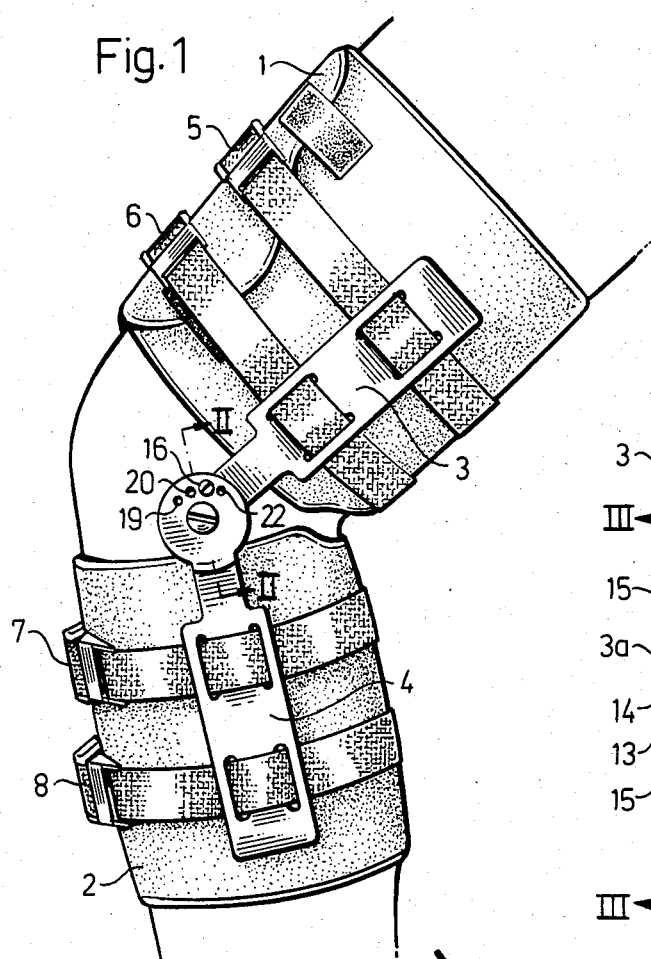
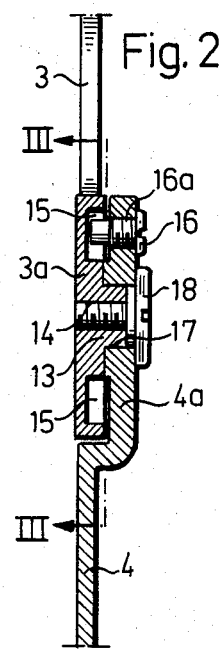
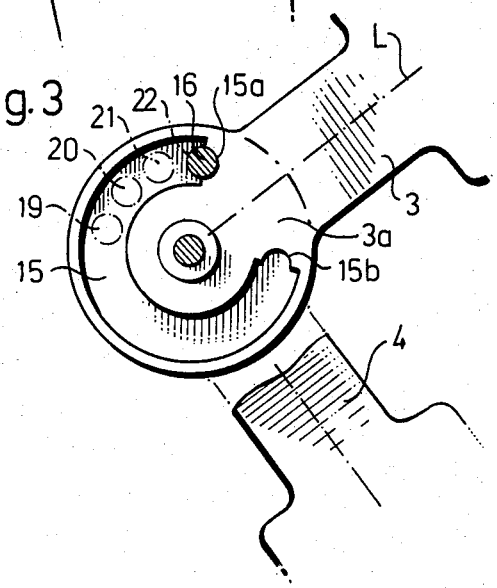

HINGE FOR KNEE JOINT BANDAGE

FIELD OF THE INVENTION this invention relates to a hinge for knee joint bandages.

In this type of knee bandage, such a hinge is arranged on each side of an injured knee, and the upper links of the hinges are secured to a support sleeve located above the knee, whereas the lower links of the hinges are secured to a similar support sleeve below the knee. The support sleeves can possibly be joined into a unit, such as a stocking, and normally, the hinges are secured by means of straps around the leg. Hereby, two desired effects are primarily achieved. On the one hand, the hinges are guided in a well-defined pivoting plane, whereby sideloads on the knee joint are reduced, and on the other hand, the angle between the lower leg and the upper leg can be limited to a desired value, normally not exceeding about 180°, in order to prevent a s.c. hyperextension of the knee joint. In certain kinds of knee injuries, or after knee operations, it is desirable to limit the maximum angle of the knee joint to considerably lower angle values. Usually, the hinges are designed so that the maximum pivot angle is adjustable by relatively simple means.

BACKGROUND OF THE INVENTION

A hinge of the kind stated above is known from U.S. Pat. No. 4,088,130, wherein two flat steel links are extended sideways in the pivoting plane at their end portions, which partially overlap each other, wherein a pivot pin connects the links to each other. At the end portion of the upper link there is a peripheral recess adjoining two abutment surfaces. One of these abutment surfaces cooperates with a fixed stop pin on the lower link to limit the maximum angle of the hinge to about 180°. The other abutment surface cooperates with a stop pin insertable into several different holes in the end portion of the lower link so as to limit the minimum angle of the knee joint. Thus, the knee joint may be locked as desired in a stretched out position, pivotable between 135° and 180°, pivotable between 90° and 180°, or pivotable between 20° and 180°.

Thus, this structure does not permit the maximum angle of the knee joint to be selected at will. Because of the extension sideways of the end portions of the links, different inner and outer hinges must be manufactured. Furthermore, the abutment surfaces and the stop pins are entirely exposed in use, and therefore the relatively sharp parts may hook into or cause damage to the environment.

Another hinge for knee joint bandages is known from U.S. Pat. No. 4,320,747, wherein two flat plastic links having essentially symmetrical end portions are used. A fixed stop pin at one of the links cooperates with an inner, concealed groove of the other link. A maximum angle between the links may in this case be selected by inserting one of several different insert pieces in the groove. Of course, such insert pieces are disadvantageous, and even in this structure different inner and outer hinges must be used.

OBJECT OF THE INVENTION

The object of the invention is to eliminate the disadvantages of the previously known hinges and to achieve a structure which permits easy adjustment of the maximum knee joint angle, which can be used either as inner or outer hinge and which consists of only a few simple parts. Nor should the hinge include any sharp or edged external portions.

SUMMARY OF THE INVENTION

These objects are achieved for a hinge of the kind described above in that the circular arcuate recess of said other link extends along an angle range substantially exceeding 180°, said recess, and two adjoining abutment surfaces, being symmetrically located in relation to the longitudinal axis of the link, and in that said one link is provided with at least two holes for said stop pin, said holes being symmetrically located in relation to the longitudinal axis thereof. Hereby, a desired maximum pivot angle can be adjusted by inserting, preferably by screwing, the stop pin into a corresponding hole, and the hinge, owing to the symmetrical arrangement of the holes and the recess, can be used on the inside as well as on the outside of the knee. Preferably, the recess is a slot or a groove, so that the stop pin is guided and pretected between the sidewalls of the slot or the groove.

The number of holes can be selected to correspond to the number of different end positions (maximum pivot angles) desired. In this respect, it is an advantage that each hole can be used for two different pivot angles, depending on whether the hinge is used on the inside or the outside of the knee. In a preferred embodiment, one of the links is provided with four different holes for the stop pin. These holes have a mutual angular displacement of 20° to 35°, preferably 27° to 30°, and the maximum end position angle between the links amounts to about 180° or somewhat less, e.g., 177.5°.

BRIEF DESCRIPTION OF THE DRAWINGS

The invention will be described further below with reference to the appended drawings, which illustrate a preferred embodiment.

FIG. 1 is a side view of a knee joint bandage provided with a hinge according to the invention;

FIG. 2 shows a section along line II—II in FIG. 1;

FIG. 3 shows a section along line III—III in FIG. 2; and

Figure 4:
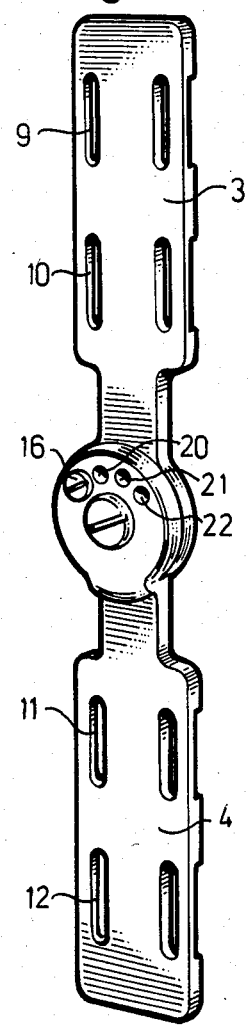
FIGS. 4 and 5 show the hinge itself in an extended position in perspective view from the front and from behind, respectively, (from the outside and the inside, respectively, in relation to the knee).
Figure 5:
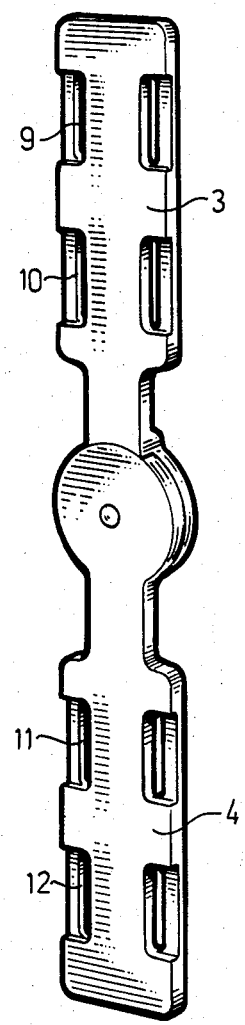

The knee joint bandage shown in FIG. 1 consists of a support sleeve 1 located above the knee and a support sleeve 2 located below the knee, there being provided, on both sides of the knee, a hinge having an upper link 3 and a lower link 4 pivotably connected to the upper link, said upper and lower links 3,4 being secured to the support sleeves 1 and 2, respectively, by means of straps 5 to 8. The elongated, flat links 3,4 (see also FIGS. 4 and 5) consist of injection molded plastics, e.g. polyamide or acetal plastic, and are on the backside (FIG. 5) provided with Velcro tapes in the wide portion having lead-through holes 9,10 and 11,12, respectively, for the straps 5,6 and 7,8, respectively, so that the links are held securely on each support sleeve 1,2 to prevent displacement or gliding.

In the region of the pivotable connection, the upper link 3 comprises in its substantially circular disk portion 3a a central, cylindrical lug 13 provided with a threaded hole 14 and a circular arcuate slot groove 15 extending symmetrically in relation to the longitudinal axis L of the link 3 along an angular range of about 270°. The depth of the slot groove 15 is at least half of the material thickness at the end portion 3a, and the width thereof exceeds the width of a stop pin 16 cooperating therewith. The ends 15a, 15b of the slot groove 15 are rounded with a radius adapted to that of the stop pin and form abutment surfaces so as to limit the maximum mutual pivoting position of the links 3,4.

The lower link 4 has a parallelly displaced, likewise circular disk end portion 4a provided with a central, circular hole 17 which fits externally on the lug 13 of the upper link 3. The links 3,4 are kept in place adjacent to each other, although pivotably to a limited extent, by means of a pivot screw 18 being screwed into the hole 14, so that its head holds the end portions 3a,4a in mutual engagement. As illustrated in FIG. 2, the stop pin 16 projects freely into the slot groove 15. Only at the end position (FIG. 3), the stop pin engages an abutment surface 15a.

By means of a threaded portion 16a, the stop pin 16 is screwed into one of four threaded holes 19,20,21,22 (see FIGS. 1,3 and 4) located symmetrically relative to the longitudinal axis L' of the lower link 4 with a mutual angular displacement of about 28° to 29°. Upon screwing the stop pin 16 into the hole 19 (FIG. 4), the links 3,4 may be almost totally straightened, namely to a mutual angle of 177.5° between the longitudinal axes L,L' of the links. When the stop pin is screwed into the hole 20 (not shown), the links (and thus the knee) can be pivoted to a maximum angle of 149.5°. Upon screwing the stop pin into the hole 21 (FIG. 1), the maximum pivot angle will be 120.5° and, finally, as shown in FIG. 3, upon screwing the stop pin 16 into the hole 22, the links may be pivoted to an angle of 92.5°. Of course, these angles may be modified at will be those skilled in the art; however, according to the invention, it is important that the holes (19 to 22) as well as the slot groove 15 be symmetrically arranged in relation to the longitudinal axes L and L', respectively, so that the hinge can be used on either side of the knee. In each case, only one abutment surface (16a in FIG. 3) is used. Only when the hinge is turned and is placed on the other side of the knee, the other abutment surface (15b in FIG. 3) will be used.

It is an essential advantage that the hinge, in spite of its versatility, consists of four separate parts only, namely, the links 3,4, the pivot screw 18 and the stop pin 16.

I claim:

1. A hinge device for a knee joint bandage, comprising first and second elongated links (3, 4) adapted to be secured to supporting sleeves (2, 3) above and below a user's knee, respectively, and connected to each other for mutual pivoting movement in a plane by means of a pivot pin (18), said links having at least partially overlapping flat end portions (3a, 4a) adjacent to said pivot pin, said links being flat over their entire length, the end portion (4a) of said second link (4) being parallely displaced by a distance substantially corresponding to the thickness of the first link, the rest of said links being arranged in a common plane, the end portion (4a) of said second link (4) being provided with a plurality of holes (19, 20, 21, 22) distributed about a circular arc about said pivot pin, a stop pin for insertion in said holes, a circular arcuate recess in the end portion of said first link, said recess having abutment means for cooperating with said stop pin to limit the end position of the pivoting movement of said links, wherein
   (a) said circular arcuate recess (15) of said first link (3) extends along an angular range substantially in excess of 180°, said recess and two adjoining abutment surfaces (15a, 15b) being symmetrically located in relation to the longitudinal axis (L) of said first link (3);
   (b) said plurality of holes (18, 20, 21, 22) selectively receiving said stop pin (16) and being symmetrically located in relation to the longitudinal axis (L') of said second link (4);
   (c) said hinge device being securable to said supporting sleeves (1, 2) on either side of either knee of the user so as to limit the maximum knee joint angle to a selectable value determined by the positioning of said stop pin in a selected one of said holes;
   (d) said recess is constituted by a slot with walls on both sides thereof.

2. A hinge device according to claim 1, wherein said slot (15) is constituted by a closed groove with bottom and side walls.

3. A hinge device according to claim 1, wherein said holes (19, 20, 21, 22) are threaded, and said stop pin (16) has a corresponding screw thread (16a) for engagement with selected ones of said holes.

4. A hinge device according to claim 1, consisting of only said links (3, 4), said pivot pin (18) and said stop pin (16).

5. A hinge device according to claim 1, wherein said angular range of said recess (15) is about 270° and said second link (4) is provided with four holes (19, 20, 21, 22) mutually angularly displaced by an angle in the range of 20° to 35°, the largest selectably maximum knee joint angle being about 180°.

6. A hinge device according to claim 5, wherein the mutual angular displacement of said holes is in th range of 27° to 30°.

* * * * *